US006540787B2

(12) United States Patent
Biegun et al.

(10) Patent No.: US 6,540,787 B2
(45) Date of Patent: Apr. 1, 2003

(54) FEMORAL COMPONENT OF A KNEE PROSTHETIC INCLUDING THREE CURVATURE RADII

(75) Inventors: Jean-François Biegun, Chaumont (FR); Pascal Marceaux, Chaumont (FR)

(73) Assignee: Aesculap (FR)

( * ) Notice: Subject to any disclaimer, the term of this patent is extended or adjusted under 35 U.S.C. 154(b) by 0 days.

(21) Appl. No.: 09/773,758

(22) Filed: Jan. 31, 2001

(65) Prior Publication Data

US 2001/0021877 A1 Sep. 13, 2001

(30) Foreign Application Priority Data

Feb. 24, 2000 (FR) .............................. 00 02312

(51) Int. Cl.[7] .................................. A61F 2/38
(52) U.S. Cl. ................. 623/20.31; 623/20.35
(58) Field of Search .................. 623/16.11, 20.14, 623/20.15, 20.21, 20.24, 20.31

(56) References Cited

U.S. PATENT DOCUMENTS

| | | | |
|---|---|---|---|
| 3,964,106 A | | 6/1976 | Hutter, Jr. et al. ............ 3/1.911 |
| 4,470,158 A | * | 9/1984 | Pappas et al. .............. 623/20.2 |
| 5,011,496 A | | 4/1991 | Forte et al. .................... 623/20 |
| 5,824,100 A | | 10/1998 | Kester et al. .................. 623/20 |
| 6,013,103 A | | 1/2000 | Kaufman et al. ............. 623/20 |
| 6,152,960 A | * | 11/2000 | Pappas ..................... 623/20.31 |
| 6,264,697 B1 | * | 7/2001 | Walker ..................... 623/20.14 |

FOREIGN PATENT DOCUMENTS

EP        0 765 645 A2    4/1997    ............. A61F/2/38

* cited by examiner

Primary Examiner—David J. Isabella
Assistant Examiner—Urmi Chattopadhyay
(74) Attorney, Agent, or Firm—Renner, Kenner, Greive, Bobak, Taylor & Weber

(57) ABSTRACT

A femoral part of a knee prosthetic of the type known as comprising three compartments, including two condyles (2) and a trochlea surface part (3) wherein the femoral part is to be anchored to the distal extremity of a femur and the external surface of the condyles is to co-operate with the upper external surface of a tibia insert such that, in a longitudinal section, the trochlea support surface (3) defines a trochlean trajectory following a first circular arc and, still in a longitudinal section, the external surface of the condyles (2) includes at least partially an intermediary circular arc (5), characterised in that in a longitudinal section, the external surface of the condyles (2) comprises an intermediary surface (5) and an extremity surface (6) both of which are a circular arc, with the intermediary circular arc (5) extending over an angle of 80° to 90°, the extremity circular arc (6) extending over an angle of 40° to 50°, the value of the curvature radius of the extremity arc (6) being strictly less than the value of the curvature radius of the intermediary arc (5).

4 Claims, 1 Drawing Sheet

FEMORAL COMPONENT OF A KNEE PROSTHETIC INCLUDING THREE CURVATURE RADII

TECHNICAL FIELD

The present invention relates to femoral parts of a knee prosthetic. It relates notably to femoral parts of a knee prosthetic of the type known as comprising three compartments, i.e. two parts which define the condyles and are separated by a trochlea surface.

These prosthetic femoral parts are implemented to co-operate with an insert often made of a material such as polyethylene, laid onto the tibia plate of a tibia part, with said co-operation taking place by means of the external surfaces of the condyles of the femoral part rolling and sliding on the upper concave surfaces of the insert.

BACKGROUND ART

A prosthetic femoral part of this type is known from the prior art, notably from the international patent application WO92/03108 of British Technology plc. With reference to a longitudinal cross-section, i.e. with reference to a section parallel to the longitudinal axis of the femur and to the longitudinal axis of the tibia with the knee flexed, this prosthetic femoral part features two circular arcs, with the first of said circular arcs corresponding to the trochlea surface and thus defining the trochlean trajectory. This radius will be designated further with the reference R1. The second circular arc of this longitudinal cross-section corresponds to the two condyles. This radius will be designated further with the reference R2.

According to the prior art, the value of radius R1 is slightly greater than the value of radius R2, generally according to a 1.2 ratio. These types of femoral parts, when used in co-operation with upper concave surfaces with a corresponding spherical shape or cylindrically circular shape, ensure a perfect congruence between the surfaces of the condyles and the surfaces of the tibia insert throughout the flexion range, i.e. between 0° and 130°. However, this type of knee prosthetic, according to the prior art features the problem that the constraints to which the ligaments and notably the upper crossed ligament, are submitted in the flexion range between 80° or 90° and 130° are very elevated.

The present invention aims to remedy this problem by means of a prosthetic femoral part which allows to decrease the constraints applied to the ligaments in the flexion range between 80° or 90° and 130°.

DISCLOSURE OF THE INVENTION

According to the invention the femoral part of a knee prosthetic, including two condyles and a trochlea surface within which a trochlean trajectory is defined in a longitudinal section, i.e. with reference to a section parallel to the longitudinal axis of the tibia and to the longitudinal axis of the femur with the knee flexed, the trochlean trajectory being a circular arc and at least part of the condyles also being a circular arc, is characterised in that in a longitudinal section the condyles comprise two circular arcs, i.e. an intermediary circular arc and an extremity circular arc. The intermediary circular arc extends between the circular arc which defines the trochlean trajectory and the extremity circular arc with the value of the curvature radius of the extremity circular arc being lesser than the value of the curvature radius of the intermediary circular arc, the intermediary circular arc extending in an angle of 80° to 90° and the extremity circular arc extending in an angle of 40° to 50°.

A perfect congruence is therefore obtained with the concave surfaces of the tibia insert having a curvature radius more or less equal to the curvature radius of the intermediary circular arc in a flexion range of 80° to 90°. However, for an increased flexion, i.e. beyond 80° or 90°, the congruence decreases such that some looseness appears between the femoral part and the tibia insert and said looseness allows for the decrease of the constraints to which the ligaments, notably the upper crossed ligament, are submitted. Knee prosthetics including a femoral part of this type can be used without harming the upper crossed ligament in the long-term.

According to a preferred method of implementing the invention, the ratio of the intermediary circular arc over the extremity circular arc stands between one and 2.5 and preferably between 1.2 and 1.8.

The invention also relates to a knee protection including a femoral part such as previously defined and a tibia insert laid onto a tibia plate, with said tibia insert including an upper concave surface which co-operates with the external surface of the condyles, as the curvature radius of the external surface of the insert is sensibly equal to the curvature radius of the intermediary circular arc.

The invention will now be described by way of example only with reference to the accompanying drawings.

PREFERRED EMBODIMENT FOR CARRYING OUT THE INVENTION

Figure 1:
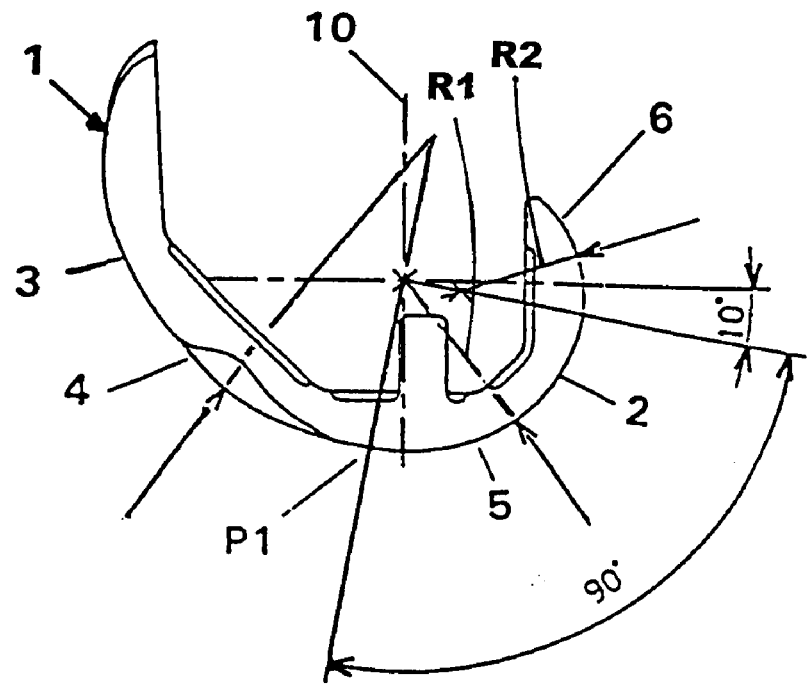
FIG. 1 is a longitudinal cross-section of the femoral part of a knee prosthetic, i.e. a section parallel to both the longitudinal axis of the tibia and the longitudinal axis of the femur, when those are not parallel, i.e. not in an extended position of the knee.
Figure 2:
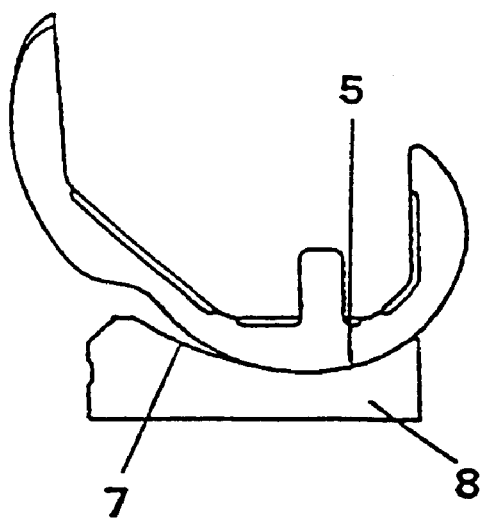
FIG. 2 is a cross-section of the femoral part of a knee prosthetic laid onto a tibia insert, according to the same longitudinal direction, with the knee in an extended position.

At FIG. 1, the femoral part 1 of a knee prosthetic comprises two condyles 2 (since the Figure is a cross-section, only one condyle appears in FIG. 1) and a trochlea support part 3 which defines a trochlean trajectory 4. Said trochlean trajectory extends up to point P1 then, beyond point P1 on the posterior side of the knee, circular arcs correspond to said condyles. In a longitudinal section, the external surface of the condyles therefore comprises a first intermediary circular arc 5 and a second extremity circular arc 6. Said first intermediary circular arc 5 extends in an angle of 90°. Said second extremity circular arc 6 extends in an angle of 40°. The value of the radius of extremity circular arc 6 is lower than the value of the radius of intermediary circular arc 5. The value of the radius of the trochlean trajectory (R1) is higher than the value of the radius of intermediary circular arc 5. The curvature radius of the upper concave surface 7 of the tibia insert 8 is sensibly identical to the curvature radii of intermediary circular arc 5.

A congruence is therefore obtained in the flexion range comprised between 0° to 90°, then the congruence between the femoral part [and the tibia insert] decreases such that looseness appears between them beyond 90°. This looseness relaxes the constraints applied to the ligaments, notably constraints applied to the upper crossed ligament. The ratio of the intermediary circular arc over the extremity circular arc equals 1.25. According to the invention, the value of this ratio must be strictly above one and may even equal two or more. The axis referenced as 10 on the figures is vertical. The condyles are positioned 10° before the axis 10, i.e. the condyles are offset by 10° from to the vertical direction.

What is claimed is:

1. A femoral part of a knee prosthetic comprising three compartments, including two condyles and a trochlea support surface wherein the femoral part is adapted to be anchored to a distal extremity of a femur and an external surface of the condyles is adapted to co-operate with an upper external surface of a tibia insert such that, in a longitudinal section, the trochlea support surface defines a trochlean trajectory following a first circular arc and, still in a longitudinal section, the external surface of the condyles includes at least an intermediary circular arc, wherein in a longitudinal section, the external surface of the condyles comprises an intermediary surface and an extremity surface both of which are circular arcs, with the intermediary circular arcs extending over an angle of 80° to 90°, the extremity circular arc extending over an angle of 40° to 50°, and the value of a curvature radius of the extremity arc being less than the value of a curvature radius of the intermediary arc.

2. Femoral part of a knee prosthetic according to claim 1, wherein the ratio of the intermediary circular arc over the extremity circular arc stands between one and 2.5.

3. Femoral part of a knee prosthetic according to claim 2, wherein the ratio of the intermediary circular arc stands between 1.2 and 1.8.

4. A knee prosthetic including a femoral part according to claim 1, and a tibia insert laid onto a tibia plate, said tibia insert having an upper concave surface which co-operates with the external surface of the condyles, as the curvature radius of the external surface of the insert is approximately equal to the curvature radius of the intermediary circular arc.

* * * * *